United States Patent [19]

Fontana et al.

[11] Patent Number: 4,814,428

[45] Date of Patent: Mar. 21, 1989

[54] METHOD OF INCREASING THE THERMAL STABILITY OF CYCLIC CARBONATE OLIGOMERS

[75] Inventors: Luca P. Fontana, Clifton Park; Thomas G. Shannon, Schenectady, both of N.Y.

[73] Assignee: General Electric Company, Schenectady, N.Y.

[21] Appl. No.: 58,103

[22] Filed: Jun. 4, 1987

[51] Int. Cl.$^4$ ............................................. C08G 63/62
[52] U.S. Cl. .................................. 528/370; 528/371; 549/201; 549/205

[58] Field of Search ................ 528/370, 371; 549/201, 549/205

[56] References Cited

U.S. PATENT DOCUMENTS 4,727,134  2/1988  Brunelle et al. ..................... 528/370

*Primary Examiner*—Harold D. Anderson
*Attorney, Agent, or Firm*—Mary A. Montebello; James C. Davis, Jr.; James Magee, Jr.

[57] ABSTRACT

The thermal stability of cyclic carbonate oligomers may be increased by treating a solution of the oligomers with an effective amount of a hydrogen halide.

11 Claims, No Drawings

METHOD OF INCREASING THE THERMAL STABILITY OF CYCLIC CARBONATE OLIGOMERS

This invention relates to methods of increasing the thermal stability of cyclic carbonate oligomers.

Cyclic carbonate oligomers are very useful in the preparation of polycarbonates. For example, U.S. Pat. Nos. 3,155,683 and 3,386,954 disclose the preparation of low molecular weight cyclic aromatic carbonate polymers and their subsequent conversion to linear polycarbonates. Furthermore, U.S. Pat. No. 4,644,053, issued to D. Brunelle et al., discloses cyclic oligomer compositions which are especially suitable for conversion to high molecular weight linear polycarbonates because of their very low inherent viscosity. For example, these mixtures of cyclic oligomers can be simultaneously polymerized with an initiator and molded to produce polycarbonate articles having the highly desirable physical properties possessed by polycarbonates prepared by conventional methods.

However, one drawback associated with polycarbonate preparation from cyclic oligomers is the chemical instability of these oligomers in the melt phase, i.e, in a molten state prior to conversion to higher molecular weight linear polycarbonates. The oligomers often undergo autopolymerization at elevated temperatures, above about 250° C., even in the absence of a polymerization initiator. It is thought that impurities present in the cyclics or introduced from the environment act as substitute initiators which induce polymerization.

The premature polymerization of the cyclic oligomers results in an undesirable increase in viscosity prior to utilization of the mixture. High initial viscosities prevent the rapid flow of the cyclic oligomer mixture into mold cavities, thereby causing considerable delays in mold processing operations.

The washing of the cyclic oligomeric mixture with a dilute solution of an acid appears to eliminate some of the impurities which cause instability in the mixture. However, even after multiple washes, residual impurities remain which continue to cause slow polymerization with an accompanying increase in viscosity, especially at temperatures of about 300° C.

It is therefore an object of the present invention to provide a means for increasing the thermal stability of cyclic oligomer mixtures.

It is a further object of the present invention to remove or neutralize impurities responsible for viscosity increase in cyclic oligomer mixtures.

It is yet another object of the present invention to provide a viscosity stabilization method for cyclic oligomers which does not interfere with subsequently utilized initiators when polymerization is required.

DETAILED DESCRIPTION OF THE INVENTION

"Thermal stability" as used herein refers to the characteristic wherein less than about 5% polymerization occurs in a cyclic carbonate oligomer mixture after the mixture has been held at 250° C. for 60 minutes; and less than about 40% polymerization occurs after the mixture has been held at 300° C. for 30 minutes. The degree of polymerization is measured by gel permeation chromatography (GPC), as described below in the examples. The measure of percent polymer formed excludes any high molecular weight polymer byproduct of the reaction used to prepare the cyclic oligomeric mixture.

Thermal stability of cyclic carbonate oligomers may be increased according to the present invention by treating the oligomers with an amount of a hydrogen halide sufficient to substantially prevent the above-mentioned polymerization.

It is to be understood that for the sake of brevity, the cyclic carbonate oligomers will hereinafter sometimes be referred to as the "cyclic oligomers" or the "cyclics mixture". Before proceeding with the details of this method, it may be useful to describe the types of materials suitable for such treatment.

The term "cyclic carbonate" as used herein includes all molecular groups containing at least one type of cyclic carbonate oligomer, e.g., dimer, trimer, tetramer, etc. These oligomers generally have degrees of polymerization from about 2 to 30. Illustrative compositions, as well as methods for their preparation, are described in detail in U.S. Pat. No. 4,644,053, incorporated herein by reference. The structural units in these oligomers generally have the formula

wherein each R is independently a divalent aliphatic, alicyclic or aromatic group, and each $Y^1$ is independently oxygen or sulfur.

The cyclic oligomer mixtures may contain organic carbonate, thiolcarbonate, and dithiolcarbonate units. Suitable R values include ethylene, propylene, and many other groups described in the above-referenced U.S. Pat. No. 4,644,053.

Generally, at least about 60% and most often at least about 80% of the total number of R values in the mixtures are aromatic groups. Most of these groups have the formula

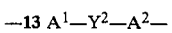

wherein each of $A^1$ and $A^2$ is a single-ring divalent aromatic group and $Y^2$ is a bridging group in which one or two atoms separate $A^1$ from $A^2$. Such R values frequently are derived from bisphenols of the formula HO—$A^1$—$Y^2$—$A^2$—OH. $A^1$ and $A^2$ generally represent unsubstituted phenylene and substituted derivatives thereof. The bridging radical $Y^2$ is most often a hydrogen group and particularly, a saturated group such as methylene, cyclohexylmethylene, and isopropylidene. The R group most often present in these oligomeric mixtures is the 2,2-bis(4-phenylene) propane radical.

Other cyclic carbonates suitable for treatment by the presently disclosed method include the cyclic heterocarbonate oligomer compositions described in copending and commonly assigned application Ser. No. 890,053, filed July 28, 1986, now U.S. Pat. No. 4,696,998, the contents of which are incorporated herein by reference. These oligomers are characterized by the presence of non-carbonate groups in the main chain. Illustrative groups include amide, ester, ether imide, ether ketone, and ether sulfone.

As mentioned briefly above, the oligomers in these mixtures generally have degrees of polymerization of from about 2 to about 30. Furthermore, the compositions have relatively low melting points and are generally liquid at temperatures above 225° C.

Methods for the preparation of cyclic carbonate oligomer mixtures are known in the art and are described in detail, for example, in the Brunelle reference described above, as well as in U.S. Pat. No. 4,696,998. For example, the cyclic oligomers may be formed by reacting a bishaloformate such as bisphenol A bischloroformate with triethylamine and aqueous sodium hydroxide. Typically, such a reaction is carried out in a non-polar solvent such as methylene chloride or chloroform. When the reaction is complete, the solution of the crude product is generally separated and washed one or more times with dilute portions of an acid, e.g., less than 1.0 M hydrochloric acid.

In the method of the present invention, treatment of the cyclics with the hydrogen halide (hereinafter alternatively referred to as the "treatment agent") is most often carried out while the cyclics are dissolved in the reaction solvent utilized for their preparation. It is thought that most of the impurities have been introduced into the solution during the formation of the cyclics. However, this process may also be used to treat cyclics which have already been separated from the reaction solvent and then re-dissolved in more solvent.

It is also thought that the impurities for the most part are anionic and may comprise phenoxide-terminated, linear carbonate oligomers. These species are by-products of the reaction used in forming the cyclic oligomers. Treatment with effective amounts of the hydrogen halide appears to neutralize these species, thereby resulting in thermal stability, as further described below.

In preferred embodiments, an effective amount of the hydrogen halide is utilized in gaseous form and is delivered into a solution of the cyclics while the solution is agitated. An "effective amount" of the hydrogen halide is defined as an amount sufficient to render the cyclic carbonates thermally stable, i.e., to substantially prevent polymerization of the oligomers under the thermal conditions defined above. The hydrogen halide level required for effectiveness depends in part on the precursors used to form the cyclic oligomers, and also depends in part on the method in which the treatment compound is introduced into the cyclics mixture. Generally, when the hydrogen halide is employed in gaseous form, about 10 to 50 mole % of hydrogen halide per total moles of cyclic oligomers present in the mixture results in thermal stabilization of the cyclic oligomers.

The minimum effective molar weight of hydrogen halide appears to be always greater than the calculated molar weight of phenoxide-terminated linear oligomers which are present in the cyclics mixture.

While in theory, no upper limit to hydrogen halide addition exists, a practical upper limit for most commercial embodiments of this invention is determined by the saturation point of the hydrogen halide in the organic solvent containing the cyclic oligomers. "Saturation point" as used herein is defined as the maximum equilibrium quantity of dissolved solute in solution at room temperature. In the absence of any cyclic oligomers dissolved in a particular solvent, the saturation point of hydrogen halides in the non-polar organic solvents used herein are well-known in the art or can be easily determined. If cyclic oligomers are present in the solvent, the solubility of the hydrogen halide will change, thus changing the saturation point. Those skilled in the art can determine the saturation point for various combinations of hydrogen halide, reaction solvent, and cyclic oligomers present without undue experimentation, since going above the saturation point results in an outflow of hydrogen halide gas from the mixture. As a general guideline, a saturation point is achieved for 1 molar weight of bisphenol A bischloroformate-based cyclic oligomers dissolved in methylene chloride when about 0.6 mole of hydrogen halide has been added per liter of solution.

The effective level of hydrogen halide addition is also related to the period of time in which the hydrogen halide is in contact with the cyclics. A particularly effective period of time for contact when about 10 mole % of hydrogen halide per total moles of cyclic oligomers is used is at least about 90 seconds. In general, longer contact periods compensate for lower levels of hydrogen halide addition, while higher levels of hydrogen halide compensate for shorter periods of contact within the above-described ranges.

In preferred embodiments, the cyclics mixture is agitated for at least about 4 to 8 minutes after addition of the hydrogen halide is complete. This additional contact time appears to further increase the thermal stability of the oligomers. Those skilled in the art may easily determine an appropriate regimen for hydrogen halide treatment by monitoring polymerization formation with gel permeation chromatography on test samples of the cyclics mixture prior to full scale treatment. Furthermore, the appropriate treatment levels and times for hydrogen halide addition in the form of an aqueous solution are discussed below.

The preferred hydrogen halide for the various embodiments of the present invention is hydrogen chloride (HCl). The hydrogen chloride is preferably utilized in gaseous form at the levels described above.

Hydrogen bromide and hydrogen iodide are also possible as treatment agents in the present invention. In gaseous form, each should be used at a molar level no lower than the calculated molar weight of phenoxide-terminated linear oligomers present in the cyclics mixture; and no higher than the saturation point of the halide.

The particular technique of introducing the gaseous hydrogen halide compound into the mixture of cyclic oligomers is not critical to the present invention and will not receive exhaustive treatment herein. The hydrogen halide gas may be supplied from any convenient source, such as a pressurized tank. A regulator with valve attachments to control gas flow may be attached to the top of the tank. Synthetic tubing connects the regulator to a dip-tube which is in turn inserted into the flask or tank containing the cyclic oligomer solution. A flowmeter attached to the regulator or along the synthetic tubing provides a constant readout of gas flow into the cyclics mixture.

As discussed above, it is preferred that the cyclics mixture be agitated, both during and after addition of the hydrogen halide. Impeller means are generally employed to provide agitation.

The rate of addition of gaseous hydrogen halide is not especially critical to the present invention and depends in part on the amount of agitation being utilized and the solids content of the mixture. The addition should be controlled in a manner which minimizes evolution of the gas to the atmosphere. For example, higher concentrations of cyclics within the organic solvent solution might require lower rates of hydrogen halide addition, unless agitation is increased. In preferred embodiments of the present invention, the hydrogen halide is added to the solution over the course of about 1 to about 10 minutes. The total amount of hydrogen halide added may be conveniently measured by the flowmeter, or by placing the gas source on a scale and simply measuring weight loss as the gas is fed into the mixture.

In order to insure effective treatment, agitation of the cyclic oligomer mixture might be continued for about 4 minutes to about 8 minutes after addition of the hydrogen halide is complete, as described above. This additional agitation period appears to result in the substantially complete neutralization of any impurities which would otherwise initiate premature polymerization of the cyclic oligomers.

As mentioned above, another embodiment of this invention calls for the addition of an aqueous solution of the hydrogen halide into the reaction mixture. It is critical to the success of this embodiment that highly concentrated hydrogen halide solutions be employed. For example, hydrogen chloride should be dissolved in an aqueous solution at about 37% by weight. Hydrobromic acid should have a concentration of about 48% by weight in water, while hydriodic acid should have a concentration of about 50% by weight in water. In general, the most effective concentration of these acids may be determined by those skilled in the art without undue experimentation.

The aqueous hydrogen halide acids are utilized at a higher molar level than in the gaseous addition embodiment described above, i.e at least about 300 mole % of hydrogen halide in solution per total moles of cyclic oligomers. The aqueous solution may be poured or pumped into the cyclic oligomer mixture by well-known means at a rate which allows the hydrogen halide to rapidly dissolve in the organic phase containing the cyclics. After addition of the the aqueous hydrogen halide is complete, the cyclic mixture is then agitated for about 4 to about 8 minutes.

After agitation is complete, the cyclic mixture treated by any of the above-described embodiments may be washed with deionized water until the pH of the aqueous phase of the mixture is determined to be neutral. Multiple washes are generally utilized. Each washing may consist of about 10 minutes of stirring, followed by another 10 minutes of phase separation. The organic phase containing the treated cyclic oligomers may be separated from the aqueous phase by well-known methods such as decantation, centrifugation, and filtration.

The cyclic oligomers remaining in the organic phase may then be isolated by any convenient method, such as steam stripping, in which the organic solvent is driven from the cyclic oligomers by high-pressure steam. Alternatively, the cyclic oligomers may be precipitated into a nonsolvent such as methanol, isopropanol, or hexane. Furthermore, a procedure often referred to as "steam crumbing" may be employed, in which the solution of cyclics is sprayed into boiling water which is under agitation. The organic solvent boils off, and the cyclics, which are insoluble in water, precipitate. The cyclics product may then be dried by well-known methods, e.g., use of a vacuum oven.

A principal advantage of this method is the very rapid thermal stabilization that can be achieved, as described in the examples below. Furthermore, treatment by the hydrogen halide does not in any way interfere with initiators which are subsequently added to the mixture of cyclic oligomers when polymerization is desired. Polycarbonates prepared from cyclic oligomeric mixtures treated by this method exhibit the same desirable physical properties as polycarbonates treated in any other manner, e.g., properties such as high tensile and impact strength, optical clarity, and good chemical resistance.

The invention is further described in the examples which follow. Parts and percentages are by weight solids unless otherwise specified.

EXAMPLES

Example 1

A set of 10.0 g samples of cyclic oligomers was used in this example. The cyclic oligomers were formed by reacting bisphenol A bischloroformate with aqueous sodium hydroxide and triethylamine in methylene chloride according to the procedure outlined in Examples 1-18 in U.S. Pat. No. 4,644,053. The cyclics mixture contained about 12% by weight high molecular weight polycarbonate polymer as measured by GPC. Samples 1-7 were each formed by dissolving 10.0 g of the solid cyclic oligomer product in 100 ml of methylene chloride in a bubbler equipped with a gas dispersion tube having a fritted disk. For each sample run, hydrogen chloride gas was delivered into the bubbler at a rate of 0.22 g/min (6 millimoles/min) for the time period indicated in Table 1 below. The cyclics mixture was rapidly agitated during the gas addition. Each solution was then washed three times with 50 mL of deionized water following the addition of the gas.

The methylene chloride in each case was then evaporated, and the residue was dried in a vacuum oven before being submitted for the thermal stability tests.

Thermal stability tests according to the standards set out above were performed by analyzing each sample on a GPC device. The results of these experiments are set out in Table 1:

TABLE 1

| | Treatment of Cyclic Carbonate Oligomers With HCl Gas[a] | | |
|---|---|---|---|
| Sample No. | HCl Delivery Time Period (minutes) | Polymer Formed[b] 1 hr/250° C. | Polymer Formed[b] 0.5 hr/300° C. |
| 1 | 0 | 32% | 58% |
| 2 | 0.5 | 4% | 29% |
| 3 | 1.0 | 1% | 13% |
| 4 | 2.0 | 1% | 6% |
| 5 | 3.0 | 1% | 7% |
| 6 | 5.0 | — | 5% |
| 7 | 10.0 | 2% | 3% |

[a]HCl rate of 0.22 g/minute.
[b]Values are within ±5%.

The above results clearly demonstrate that treatment with hydrogen chloride substantially increases the thermal stability of the cyclic oligomers. Based on this experiment, about 0.44 g (12 millimoles) added over a period of about 2 minutes appeared to be an especially satisfactory treatment schedule, resulting in a 300° C. stability value of 6%.

There was no agitation of the solution after the addition of hydrogen chloride in these particular examples. Such agitation would have resulted in thermal stabilization being achieved at even lower levels of HCl, as demonstrated below in Example 2.

After the hydrogen chloride treatment, each sample was polymerized with an initiator. Polymerization was not adversely affected in any manner by the treatment, and the molecular weight of the polycarbonates formed was equivalent to that achieved without the hydrogen chloride treatment.

A saturation point of hydrogen chloride in the cyclic oligomer solution was reached when about 0.77 g (21 millimoles) had been added, as evidenced by the outflow of gaseous hydrogen chloride.

Example 2

Samples 8–10 were each prepared by dissolving 10.0 grams of the cyclics material used in Example 1 in 100 ml of methylene chloride. Hydrogen chloride gas was fed into a bubbler containing this solution at a rate of about 1.2 g/min (33 millimoles/min) until the amount of hydrogen chloride indicated in Table 2 had been added.

After the addition of hydrogen chloride gas in each sample, each solution was agitated for another 5 minutes with a magnetic stirrer. Each solution was then washed three times with 50 ml of deionized water. The methylene chloride was then evaporated and the residue was dried in a vacuum oven before being submitted for the thermal stability test.

Each sample was heated at 300° C. for 30 minutes, followed by cooling to room temperature and analysis by GPC. The results are shown on Table 2 below:

TABLE 2

| HCl Gaseous Treatment Followed by Agitation Of the Cyclics Solution | | |
|---|---|---|
| Sample No. | Amount of HCl (grams) | % Polymer Formation[a] |
| 8 | 0.1 | 8% |
| 9 | 0.2 | 1% |
| 10 | 0.3 | 0% |

[a]After 30 minutes at 300° C.

The results in Table 2 demonstrate that lower levels of hydrogen chloride gas within the range described above are effective in thermally stabilizing the cyclic oligomer mixtures when agitation of the cyclics solution follows the addition of the gas. Each of Samples 8–10 were thermally stable according to the standard outlined above. Although the 250° C. heating test was not used in this example, samples meeting the 300° C. test always pass the 250° C. test.

Example 3

This example demonstrates the feasibility of treatment with the hydrogen halide in the form of a highly concentrated aqueous solution.

For Sample 11, 10.0 g of a bisphenol-A bischloroformate-based cyclic oligomer product was dissolved in 50 mL of methylene chloride. As noted above, the cyclic oligomers as formed were thermally unstable.

For Sample 12, about 10.0 g of another bisphenol-A bischloroformate-based cyclic oligomeric product (having greater initial thermal instability than Sample 11) was dissolved in about 50 mL of methylene chloride.

Each cyclics solution was washed with water and dilute portions of hydrochloric acid, followed by three consecutive washes with 75 ml of concentrated hydrochloric acid (37% by weight in water).

The two-phase mixture in each sample was then washed with deionized water until the discarded washings exhibited a neutral pH. The organic layer was then separated and rotoevaporated to obtain the cyclics product.

Thermal stability tests were conducted as described above. For Sample 11, 5% polymerization occurred after 60 minutes at 250° C., and 8% polymerization occurred after 30 minutes at 300° C. For Sample 12, 1% polymerization occurred during the 250° C. test, while 37% polymerization occurred during the 300° C. test.

The method of the present invention has been used to thermally stabilize various batches of cyclic oligomers which initially exhibited a wide range of thermal instability ranging from 0% polymerization at 250° C. over 60 minutes to nearly 100% polymerization in 30 minutes at the same temperature. Thermal stability was consistently obtained for each of those samples after treatment with the hydrogen halide compound.

Modifications and variations of the present invention are possible in light of the above teachings. It should therefore be understood that changes made in particular embodiments described herein are within the full intended scope of the invention defined by the appended claims.

What is claimed is:

1. A method of increasing thermal stability of cyclic carbonate oligomers, comprising treating an organic solvent solution of the cyclic carbonate oligomers with an amount of a hydrogen halide sufficient to substantially prevent polymerization of the oligomers.

2. The method of claim 1 wherein the hydrogen halide in gaseous form is delivered into the solution of the cyclics.

3. The method of claim 2 wherein the hydrogen halide is hydrogen chloride.

4. The method of claim 3 wherein about 10 to about 50 mole % of hydrogen chloride per total moles of cyclic oligomers is added to the solution.

5. The method of claim 3 wherein the addition of hydrogen chloride is followed by continued agitation of the mixture for about 4 to about 8 minutes.

6. The method of claim 5 wherein the solvent of said solution is a chlorinated aliphatic hydrocarbon.

7. The method of claim 6 wherein the cyclic oligomers are the product of a reaction of a bishaloformate with a tertiary amine and an aqueous metal hydroxide solution.

8. The method of claim 7 wherein bisphenol A bischloroformate is reacted with triethylamine and aqueous sodium hydroxide.

9. The method of claim 1 wherein the organic solvent solution is washed with water after treatment with the hydrogen halide, followed by separation of the cyclic oligomers from the solution.

10. The method of claim 1 wherein the hydrogen halide is hydrogen chloride dissolved in an aqueous solution at about 37% by weight.

11. The method of claim 10 wherein about 300 mole % of hydrogen chloride per total moles of cyclic oligomers is added to the solution of cyclic oligomers.

* * * * *